US012691223B2

(12) United States Patent
Kiani

(10) Patent No.: US 12,691,223 B2
(45) Date of Patent: Jul. 28, 2026

(54) SEPSIS MONITOR

(71) Applicant: MASIMO CORPORATION, Irvine, CA (US)

(72) Inventor: Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/641,190

(22) Filed: Apr. 19, 2024

(65) Prior Publication Data

US 2024/0269384 A1      Aug. 15, 2024

Related U.S. Application Data

(63) Continuation of application No. 16/299,004, filed on Mar. 11, 2019, now abandoned, which is a continuation of application No. 14/191,925, filed on Feb. 27, 2014, now Pat. No. 10,226,576, which is a continuation of application No. 13/100,172, filed on May 3, 2011, now Pat. No. 8,663,107, which is a (Continued)

(51) Int. Cl.
| | |
|---|---|
| *A61M 5/172* | (2006.01) |
| *A61B 5/00* | (2006.01) |
| *A61B 5/0205* | (2006.01) |
| *A61B 5/022* | (2006.01) |
| *A61B 5/0245* | (2006.01) |
| *A61B 5/08* | (2006.01) |
| *A61B 5/1455* | (2006.01) |
| *A61B 7/04* | (2006.01) |

(52) U.S. Cl.
CPC ......... *A61M 5/1723* (2013.01); *A61B 5/0205* (2013.01); *A61B 5/022* (2013.01); *A61B 5/02455* (2013.01); *A61B 5/08* (2013.01); *A61B 5/14551* (2013.01); *A61B 5/412* (2013.01); *A61B 5/6826* (2013.01); *A61B 5/6838* (2013.01); *A61B 7/04* (2013.01); *A61B 5/082* (2013.01); *A61B 2560/0276* (2013.01)

(58) Field of Classification Search
CPC ... A61B 5/0205; A61B 5/022; A61B 5/02455; A61B 5/08; A61B 5/14551; A61B 5/412; A61B 5/6826; A61B 5/6838; A61B 5/082; A61B 7/04; A61M 5/1723
See application file for complete search history.

(56) References Cited

U.S. PATENT DOCUMENTS

| | | | |
|---|---|---|---|
| 4,248,241 A | 2/1981 | Tacchi | |
| 4,869,253 A | 9/1989 | Craig, Jr. et al. | |

(Continued)

OTHER PUBLICATIONS

US 2024/0016391 A1, 01/2024, Lapotko et al. (withdrawn)

(Continued)

*Primary Examiner* — Amanda L Steinberg
(74) *Attorney, Agent, or Firm* — Knobbe, Martens, Olson & Bear, LLP

(57) ABSTRACT

Sensors are attached to a living being so as to generate corresponding sensor signals. A monitor is in communications with the sensors so as to derive physiological parameters responsive to the sensor signals. Predetermined limits are applied to the physiological parameters. At least one indicator responsive to the physiological parameters and the predetermined limits signal the onset of a sepsis condition in the living being.

11 Claims, 6 Drawing Sheets

Related U.S. Application Data continuation of application No. 11/803,936, filed on May 15, 2007, now Pat. No. 7,941,199.

(60) Provisional application No. 60/800,629, filed on May 15, 2006.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Hink et al. |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |
| 5,452,717 | A | 9/1995 | Branigan et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,171,258 | B1 | 1/2001 | Karakasoglu et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |

(56) References Cited

U.S. PATENT DOCUMENTS

| | | | |
|---|---|---|---|
| 6,721,585 B1 | 4/2004 | Parker |
| 6,725,075 B2 | 4/2004 | Al-Ali |
| 6,728,560 B2 | 4/2004 | Kollias et al. |
| 6,733,464 B2 | 5/2004 | Olbrich et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,860,266 B2 | 3/2005 | Blike |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,034,692 B2 | 4/2006 | Hickle |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,081,095 B2 | 7/2006 | Lynn et al. |
| D526,719 S | 8/2006 | Richie, Jr. et al. |
| 7,090,648 B2 | 8/2006 | Sackner et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,207,964 B2 | 4/2007 | Davidner et al. |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,252,637 B2 | 8/2007 | Ebner et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,513,875 B2 | 4/2009 | Kushnir et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,536,214 B2 | 5/2009 | Myers et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,668,579 B2 | 2/2010 | Lynn |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,758,503 B2 | 7/2010 | Lynn et al. |
| 7,761,127 B2 | 7/2010 | Al-Ali et al. |
| 7,761,128 B2 | 7/2010 | Al-Ali et al. |

(56) References Cited

U.S. PATENT DOCUMENTS

| | | | |
|---|---|---|---|
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,811,279 | B2 | 10/2010 | John |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| 8,086,323 | B2 | 12/2011 | Reghabi et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,335,550 | B2 | 12/2012 | Segman |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,560,059 | B2 | 10/2013 | Hoarau et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |

(56)                References Cited

U.S. PATENT DOCUMENTS

| | | | |
|---|---|---|---|
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,692 | B2 | 4/2017 | Lamego et al. |
| 9,622,693 | B2 | 4/2017 | Diab |
| D788,312 | S | 5/2017 | Al-Ali et al. |
| 9,636,055 | B2 | 5/2017 | Al Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |

(56)　　　　References Cited

U.S. PATENT DOCUMENTS

| | | | |
|---|---|---|---|
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |

(56) References Cited

U.S. PATENT DOCUMENTS

| | | | |
|---|---|---|---|
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,061,585 S | 2/2025 | Indorf |
| D1,063,893 S | 2/2025 | DeJong et al. |
| 12,220,207 B2 | 2/2025 | Telfort et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| D1,068,656 S | 4/2025 | Trevisan et al. |
| D1,071,195 S | 4/2025 | Seung |
| D1,072,836 S | 4/2025 | Indorf |
| D1,072,837 S | 4/2025 | Ahmed et al. |
| 12,272,445 B1 | 4/2025 | Kiani |
| D1,078,689 S | 6/2025 | Hwang |
| D1,079,020 S | 6/2025 | Hwang |
| 12,336,796 B2 | 6/2025 | Al-Ali |
| D1,083,653 S | 7/2025 | DeJong et al. |
| D1,085,102 S | 7/2025 | Indorf et al. |
| 12,362,596 B2 | 7/2025 | Barker et al. |
| 12,390,114 B2 | 8/2025 | Novak, Jr. et al. |
| D1,092,244 S | 9/2025 | DeJong et al. |
| D1,093,406 S | 9/2025 | Indorf et al. |

(56) References Cited

U.S. PATENT DOCUMENTS

| | | | |
|---|---|---|---|
| D1,094,735 S | 9/2025 | DeJong et al. | |
| D1,095,288 S | 9/2025 | Lim | |
| D1,095,483 S | 9/2025 | DeJong et al. | |
| 12,433,524 B2 | 10/2025 | Al-Ali et al. | |
| 12,440,128 B2 | 10/2025 | Al-Ali et al. | |
| 2001/0034477 A1 | 10/2001 | Mansfield et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0103454 A1 | 8/2002 | Sackner et al. | |
| 2002/0133080 A1 | 9/2002 | Apruzzese et al. | |
| 2003/0000522 A1* | 1/2003 | Lynn | A61B 5/145 |
| | | | 128/200.24 |
| 2003/0013975 A1 | 1/2003 | Kiani | |
| 2003/0018243 A1 | 1/2003 | Gerhardt et al. | |
| 2003/0120182 A1 | 6/2003 | Wilkinson et al. | |
| 2003/0144582 A1 | 7/2003 | Cohen et al. | |
| 2003/0156288 A1 | 8/2003 | Barnum et al. | |
| 2003/0181815 A1* | 9/2003 | Ebner | A61B 5/412 |
| | | | 600/483 |
| 2003/0191373 A1 | 10/2003 | Bilke | |
| 2003/0208113 A1 | 11/2003 | Mault et al. | |
| 2003/0212312 A1 | 11/2003 | Coffin, IV et al. | |
| 2003/0214409 A1 | 11/2003 | Hickle | |
| 2004/0039295 A1 | 2/2004 | Olbrich et al. | |
| 2004/0078219 A1 | 4/2004 | Kaylor et al. | |
| 2004/0106163 A1 | 6/2004 | Workman, Jr. et al. | |
| 2004/0186410 A1 | 9/2004 | Davidner et al. | |
| 2004/0236229 A1 | 11/2004 | Freeman et al. | |
| 2005/0001728 A1 | 1/2005 | Appelt et al. | |
| 2005/0038332 A1 | 2/2005 | Saidara et al. | |
| 2005/0054942 A1 | 3/2005 | Melker et al. | |
| 2005/0055276 A1 | 3/2005 | Kiani et al. | |
| 2005/0065556 A1 | 3/2005 | Reghabi et al. | |
| 2005/0101841 A9 | 5/2005 | Kaylor et al. | |
| 2005/0143632 A1 | 6/2005 | Elaz et al. | |
| 2005/0148832 A1 | 7/2005 | Reghabi et al. | |
| 2005/0234317 A1 | 10/2005 | Kiani | |
| 2005/0277912 A1 | 12/2005 | John | |
| 2005/0288571 A1 | 12/2005 | Perkins et al. | |
| 2006/0020179 A1 | 1/2006 | Anderson et al. | |
| 2006/0073719 A1 | 4/2006 | Kiani | |
| 2006/0155176 A1 | 7/2006 | Ebner et al. | |
| 2006/0161054 A1 | 7/2006 | Reuss et al. | |
| 2006/0189871 A1 | 8/2006 | Al-Ali et al. | |
| 2006/0200009 A1* | 9/2006 | Wekell | A61B 5/7275 |
| | | | 600/509 |
| 2006/0276695 A9 | 12/2006 | Lynn et al. | |
| 2007/0024946 A1 | 2/2007 | Panasyuk et al. | |
| 2007/0032733 A1 | 2/2007 | Burton | |
| 2007/0073116 A1 | 3/2007 | Kiani et al. | |
| 2007/0093701 A1 | 4/2007 | Myers et al. | |
| 2007/0100213 A1 | 5/2007 | Dossas et al. | |
| 2007/0129647 A1 | 6/2007 | Lynn | |
| 2007/0180140 A1 | 8/2007 | Welch et al. | |
| 2007/0191697 A1* | 8/2007 | Lynn | A61B 5/08 |
| | | | 600/323 |
| 2007/0219434 A1 | 9/2007 | Abreu | |
| 2007/0244377 A1 | 10/2007 | Cozad et al. | |
| 2007/0282212 A1 | 12/2007 | Sierra et al. | |
| 2008/0051764 A1 | 2/2008 | Dent et al. | |
| 2008/0064965 A1 | 3/2008 | Jay et al. | |
| 2008/0094228 A1 | 4/2008 | Welch et al. | |
| 2008/0103375 A1 | 5/2008 | Kiani | |
| 2008/0118782 A1 | 5/2008 | Heller et al. | |
| 2008/0221408 A1 | 9/2008 | Hoarau et al. | |
| 2008/0221418 A1 | 9/2008 | Al-Ali et al. | |
| 2008/0286763 A1 | 11/2008 | Russwurm et al. | |
| 2008/0306353 A1 | 12/2008 | Douglas et al. | |
| 2009/0036759 A1 | 2/2009 | Ault et al. | |
| 2009/0069642 A1 | 3/2009 | Gao et al. | |
| 2009/0093687 A1 | 4/2009 | Telfort et al. | |
| 2009/0095926 A1 | 4/2009 | MacNeish, III | |
| 2009/0163776 A1* | 6/2009 | Inbar | G16H 50/70 |
| | | | 600/301 |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2009/0299154 A1 | 12/2009 | Segman | |
| 2010/0004518 A1 | 1/2010 | Vo et al. | |
| 2010/0030040 A1 | 2/2010 | Poeze et al. | |
| 2010/0099964 A1 | 4/2010 | O'Reilly et al. | |
| 2010/0234718 A1 | 9/2010 | Sampath et al. | |
| 2010/0270257 A1 | 10/2010 | Wachman et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0082711 A1 | 4/2011 | Poeze et al. | |
| 2011/0087081 A1 | 4/2011 | Kiani et al. | |
| 2011/0118561 A1 | 5/2011 | Tari et al. | |
| 2011/0125060 A1 | 5/2011 | Telfort et al. | |
| 2011/0137297 A1 | 6/2011 | Kiani et al. | |
| 2011/0172498 A1 | 7/2011 | Olsen et al. | |
| 2011/0208015 A1 | 8/2011 | Welch et al. | |
| 2011/0230733 A1 | 9/2011 | Al-Ali | |
| 2012/0123231 A1 | 5/2012 | O'Reilly | |
| 2012/0165629 A1 | 6/2012 | Merritt et al. | |
| 2012/0209082 A1 | 8/2012 | Al-Ali | |
| 2012/0209084 A1 | 8/2012 | Olsen et al. | |
| 2012/0226117 A1 | 9/2012 | Lamego et al. | |
| 2012/0283524 A1 | 11/2012 | Kiani et al. | |
| 2013/0023775 A1 | 1/2013 | Lamego et al. | |
| 2013/0041591 A1 | 2/2013 | Lamego | |
| 2013/0060147 A1 | 3/2013 | Welch et al. | |
| 2013/0096405 A1 | 4/2013 | Garfio | |
| 2013/0096936 A1 | 4/2013 | Sampath et al. | |
| 2013/0243021 A1 | 9/2013 | Siskavich | |
| 2013/0296672 A1 | 11/2013 | O'Neil et al. | |
| 2013/0324808 A1 | 12/2013 | Al-Ali et al. | |
| 2013/0331660 A1 | 12/2013 | Al-Ali et al. | |
| 2013/0345921 A1 | 12/2013 | Al-Ali et al. | |
| 2014/0012100 A1 | 1/2014 | Al-Ali et al. | |
| 2014/0051953 A1 | 2/2014 | Lamego et al. | |
| 2014/0120564 A1 | 5/2014 | Workman et al. | |
| 2014/0121482 A1 | 5/2014 | Merritt et al. | |
| 2014/0127137 A1 | 5/2014 | Bellott et al. | |
| 2014/0163344 A1 | 6/2014 | Al-Ali | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0180160 A1 | 6/2014 | Brown et al. | |
| 2014/0187973 A1 | 7/2014 | Brown et al. | |
| 2014/0213864 A1 | 7/2014 | Abdul-Hafiz et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0288400 A1 | 9/2014 | Diab et al. | |
| 2014/0316217 A1 | 10/2014 | Purdon et al. | |
| 2014/0316218 A1 | 10/2014 | Purdon et al. | |
| 2014/0316228 A1 | 10/2014 | Blank et al. | |
| 2014/0323825 A1 | 10/2014 | Al-Ali et al. | |
| 2014/0323897 A1 | 10/2014 | Brown et al. | |
| 2014/0323898 A1 | 10/2014 | Purdon et al. | |
| 2014/0330098 A1 | 11/2014 | Merritt et al. | |
| 2014/0357966 A1 | 12/2014 | Al-Ali et al. | |
| 2015/0005600 A1 | 1/2015 | Blank et al. | |
| 2015/0011907 A1 | 1/2015 | Purdon et al. | |
| 2015/0032029 A1 | 1/2015 | Al-Ali et al. | |
| 2015/0038859 A1 | 2/2015 | Dalvi et al. | |
| 2015/0073241 A1 | 3/2015 | Lamego | |
| 2015/0080754 A1 | 3/2015 | Purdon et al. | |
| 2015/0087933 A1 | 3/2015 | Gibson et al. | |
| 2015/0087936 A1 | 3/2015 | Al-Ali et al. | |
| 2015/0094546 A1 | 4/2015 | Al-Ali | |
| 2015/0099950 A1 | 4/2015 | Al-Ali et al. | |
| 2015/0101844 A1 | 4/2015 | Al-Ali et al. | |
| 2015/0106121 A1 | 4/2015 | Muhsin et al. | |
| 2015/0112151 A1 | 4/2015 | Muhsin et al. | |
| 2015/0165312 A1 | 6/2015 | Kiani | |
| 2015/0196249 A1 | 7/2015 | Brown et al. | |
| 2015/0216459 A1 | 8/2015 | Al-Ali et al. | |

(56) References Cited

U.S. PATENT DOCUMENTS

| | | |
|---|---|---|
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0201623 A1 | 7/2019 | Kiani |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329993 A1 | 10/2020 | Al-Ali et al. |
| 2021/0022628 A1 | 1/2021 | Telfort et al. |
| 2021/0104173 A1 | 4/2021 | Pauley et al. |
| 2021/0117525 A1 | 4/2021 | Kiani et al. |
| 2021/0161465 A1 | 6/2021 | Barker et al. |
| 2021/0236729 A1 | 8/2021 | Kiani et al. |
| 2021/0275101 A1 | 9/2021 | Vo et al. |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |

(56) References Cited

U.S. PATENT DOCUMENTS

| 2021/0402110 A1 | 12/2021 | Pauley et al. |
| 2022/0039707 A1 | 2/2022 | Sharma et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0255764 A1 | 8/2025 | Stead |
| 2025/0278512 A1 | 9/2025 | Koo et al. |
| 2025/0281059 A1 | 9/2025 | Avendano |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |

OTHER PUBLICATIONS

Angus, D.C., MD, MPH, FCCM, et al., "Epidemiology of Severe Sepsis in the United States: Analysis of Incidence, Outcome, and Associated Cost of Care," Critical Care Medicine, vol. 29, No. 7, pp. 1303-1310.

Dellinger, R.P., MD, et al., "Surviving Sepsis Campaign Guidelines for Management of Severe Sepsis and Septic Shock," Critical Care Medicine, vol. 32, No. 3, pp. 858-873.

Masimo, "SpCO™ Pulse CO-Oximetry™", pp. 1-4 (2005).

Ohashi, K., et al., "Elevated Methemoglobin in Patients with Sepsis," ACTA Anaesthesiologica Scandinavica, 42, pp. 713-716 (1998).

"Plasma Carbon Monoxide Levels In Pediatrics Sepsis Syndrome," The Internet Journal of Pediatrics and Neonatology, vol. 2, No. 2, 11 pages (2002), downloaded and printed from the World Wide Web on Oct. 14, 2005, http://www.ispub.com/ostia/index.php?xmlFilePath= journals/ijpn/vol2n2/sepsis.XML.

"Septic Shock: An Analysis of Outcomes for Patients with Onset on Hospital Wards Versus Intensive Care Units," Critical Care Medicine, vol. 26(6), 9 pages (Jun. 1998), downloaded and printed from the World Wide Web on Feb. 1, 2006, www.ccmjournal.com/pt/re/ccm/fulltext.00003246-199806000-00019.htm;jsessionid=.

* cited by examiner

SEPSIS MONITOR

CROSS-REFERENCE TO RELATED APPLICATIONS

The present application claims priority benefit under 35 U.S.C. § 120 to, and is a continuation of U.S. patent application Ser. No. 16/299,004, filed Mar. 11, 2019 entitled "Sepsis Monitor" which is a continuation of U.S. patent application Ser. No. 14/191,925, filed Feb. 27, 2014 entitled "Sepsis Monitor", which is a continuation of U.S. patent application Ser. No. 13/100,172, filed May 3, 2011 entitled "Sepsis Monitor", now U.S. Pat. No. 8,663,107, which is a continuation of U.S. patent application Ser. No. 11/803,936, filed May 15, 2007, entitled "Sepsis Monitor", now U.S. Pat. No. 7,941,199, which claims priority benefit under 35 U.S.C. § 119(e) from U.S. Provisional Application No. 60/800,629, filed May 15, 2006, entitled "Septic Shock Monitor". The present application also incorporates the foregoing disclosures herein by reference.

BACKGROUND OF THE INVENTION

Sepsis is a serious medical condition caused by the body's response to an infection. The source of the infection can be any of a number of places throughout the body. Bacterial infections are the most common cause of sepsis, but sepsis can also be caused by fungal, parasitic, or viral infections. Toxins produced by an untreated or inadequately treated infection circulate in the bloodstream causing damage, for example, to the brain, heart, lungs, kidneys and liver. Severe sepsis can result in septic shock, a medical emergency in which the organs and tissues of the body are not receiving an adequate flow of blood.

SUMMARY OF THE INVENTION

The signs and symptoms of sepsis may be subtle. The unacceptably low survival rate of severe sepsis indicates that current patient identification strategies may be lacking. For example, conventional patient monitors give insufficient advance warning of deteriorating patient health or the onset of potentially serious physiological conditions resulting from sepsis. Advantageously, a sepsis monitor noninvasively measures patient condition so as to provide caregivers with an advanced warning or prediction of the onset sepsis. A sepsis monitor may also be configured to provide automatic intervention or treatment of sepsis.

SIRS (systemic inflammatory response syndrome) refers to the systemic activation of the body's immune response, such as from sepsis. SIRS is manifested by, for example, the presence of more than one of a temperature greater than 38° C. or less than 36° C.; a heart rate greater than 90 beats/min.; and a respiration rate greater than 20 breaths/min. Thus, in an embodiment, a sepsis monitor is responsive to more than one of pulse rate, respiration rate and temperature.

Sepsis also results in large amounts of nitrous oxide (NO) released into the blood. It has been shown that NO functions, in part, as a killer molecule that is activated by immune cells. The overproduction of NO during sepsis induces excessive vascular relaxation and a profound hypotension that is also a characteristic feature of sepsis. NO interacts rapidly with hemoglobin to form methemoglobin (HbMet). Thus, HbMet can function as a marker for NO generation in patients with sepsis. Further, endogenously produced CO functions as a messenger molecule as part of a complex cascade of mediators resulting from sepsis. A portion of the endogenous CO is exhaled and a portion is present as carboxyhemoglobin (HbCO). Thus, in an embodiment, a sepsis monitor is responsive to one or more of HbCO, HbMet and blood pressure.

In an embodiment, sepsis monitoring is based upon one or more physiological parameters and associated parameter limits, trends, patterns and variability, alone or in combination. The physiological parameters may include: blood parameters derived from an optical sensor including one or more of oxygen saturation ($SpO_2$), pulse rate, HbCO and HbMet; respiration rate (RR) derived from an acoustic sensor or a capnography sensor, as examples; noninvasive blood pressure (NIBP) derived from a blood pressure sensor, such as an inflatable cuff and corresponding acoustic sensor, a continuous NIBP (CNIBP) measurement device or an intelligent cuff inflation (ICI) device, to name a few; and temperature manually measured or derived from a thermistor or other temperature transducer.

One aspect of a sepsis monitor is sensors attached to a living being so as to generate corresponding sensor signals. A monitor is in communications with the sensors so as to derive physiological parameters responsive to the sensor signals. Predetermined limits are applied to the physiological parameters. At least one indicator responsive to the physiological parameters and the predetermined limits signal the onset of a sepsis condition in the living being.

Another aspect of a sepsis monitor is identifying physiological parameters indicative of an onset of a sepsis condition in a living being. Sensor signals are generated that are responsive to the physiological parameters. The physiological parameters are computed from the sensor signals. Predetermined rules are applied to the physiological parameters so as to determine the onset of the sepsis condition. An indicator signals the potential existence and likely nonexistence of the sepsis condition.

DETAILED DESCRIPTION OF THE PREFERRED EMBODIMENT

Figure 1:
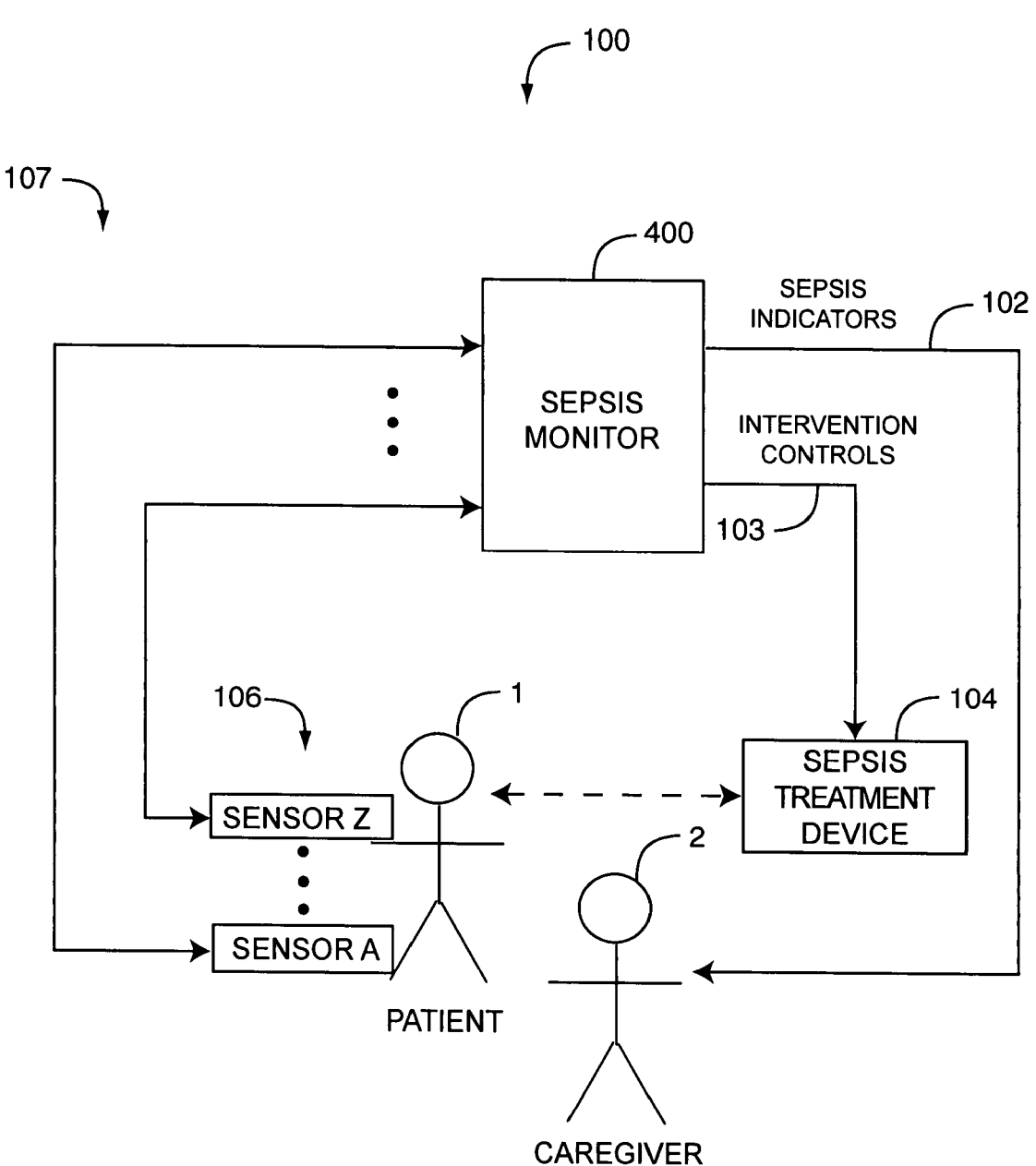
FIG. 1 is a general block diagram of a sepsis monitoring system.

FIG. 1 illustrates a sepsis monitoring system 100 having one or more sensors 106 generating sensor signals 107 in response to physiological states of a living being, such as a patient 1. A sepsis monitor 400 processes the sensor signals 107 and generates sepsis indicators 102 or intervention controls 103 or both, in response. In an open-loop configuration, one or more sepsis indicators 102 are observed by a caregiver 2, who administers treatment in response. Alternatively, or in addition, the caregiver 2 initiates, pauses, halts or adjusts the settings of a sepsis treatment device 104 in response to the sepsis indicators 102. In an embodiment, the sepsis indicators 102 signal one or more of a prediction of the onset of sepsis, a sepsis condition, a prediction of the onset of septic shock and a septic shock condition. In a closed-loop configuration, the sepsis treatment device 104 is responsive to one or more intervention controls 103 so as to affect the treatment of the patient 1, including, for example, initiating, pausing, halting or adjusting the dosage of administered drugs. In an embodiment, the intervention controls 103 are responsive to one or more of a prediction of the onset of sepsis, a sepsis condition, a prediction of the onset of septic shock and a septic shock condition.

As shown in FIG. 1, the sepsis treatment device 104 may be a drug infusion device, a medical gas inhalation device or a ventilation device to name a few. Drug infusion device and gas inhalation device control is described in U.S. patent application Ser. No. 11/654,904, filed Jan. 17, 2007, entitled Drug Administration Controller and incorporated by reference herein. Closed loop respirator control is described in U.S. patent application Ser. No. 11/585,678, filed Oct. 23, 2006, entitled Robust Ventilator Control and incorporated by reference herein.

As shown in FIG. 1, sensors 106 provide noninvasive measurements and include, for example, an optical sensor attached to a tissue site, such as a fingertip, for measuring one or more blood parameters. Noninvasive sensors 106 may also include acoustic sensors, blood pressure cuffs, ECG or EEG electrodes, $CO_2$ measuring capnography sensors and temperature sensors to name a few. The sepsis monitor 400 is responsive to sensors signals 107 so as to generate parameter measurements, which may include $SpO_2$, pulse rate, perfusion index, perfusion variability index, HbCO, HbMet, total hemoglobin, fractional saturation, glucose, cyanide, respiration rate, blood pressure, $CO_2$, bilirubin, lung volume, cardiac output, temperature, consciousness and hydration measures, among other parameters. Such parameters may be measured intermittently or continuously. Although sensors 106 are described above with respect to noninvasive technologies, sensors 106 may be invasive or noninvasive. Invasive measurements may require a person to prepare a blood or tissue sample, which is then processed by an instrument or testing device, with the result read from the instrument or device and manually entered into the sepsis monitor 400.

The sepsis monitor 400 may be a single instrument incorporating various hardware, software, circuits and code for processing sensor signals, deriving physiological parameters and processing those parameters to generate the indicators and controls described above. Alternatively, the sepsis monitor 400 may integrate one or more standalone instruments or plug-ins, each of which process specific sensor signals and derive particular physiological parameters. These may include blood parameter monitors, respiration rate monitors, blood pressure monitors, ECG and EEG monitors and capnometers, as a few examples.

In an embodiment, sensors 106 include a multiple wavelength optical sensor, such as described in U.S. patent application Ser. No. 11/376,013, filed Mar. 1, 2006 and entitled Multiple Wavelength Sensor Emitters; and the sepsis monitor 400 incorporates a patient monitor, such as described in U.S. patent application Ser. No. 11/367,033, filed Mar. 1, 2006 and entitled Noninvasive Multi-Parameter Patient Monitor, both patent applications assigned to Masimo Laboratories, Irvine, CA and both incorporated by reference herein.

In an embodiment, sensors 106 and measurement devices 108 include multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters. The Rainbow™ sensors and RAD-57™ and Radical- 7™ monitors are available from Masimo Corporation, Irvine, CA. In an embodiment, sensors 106 include a pulse oximetry sensor, such as described in U.S. Pat. No. 5,782,757 entitled Low Noise Optical Probes and the sepsis monitor 400 incorporates a pulse oximeter, such as described in U.S. Pat. No. 5,632,272 entitled Signal Processing Apparatus, both assigned to Masimo Corporation, Irvine, CA and both incorporated by reference herein. In other embodiments, sensors 106 also include any of LNOP® adhesive or reusable sensors, SofTouch™ sensors, Hi-Fi Trauma™ or Blue™ sensor all available from Masimo Corporation, Irvine, CA. Further, the sepsis monitor 400 may also include any of Radical®, SatShare™, Rad-9™, Rad-5™, Rad-5v™ or PPO+™ Masimo SET® pulse oximeters all available from Masimo Corporation, Irvine, CA.

In another embodiment, the sepsis monitor 400 and the sepsis treatment device 104 are incorporated within a single unit. For example, the sepsis monitor 400 and treatment device 104 may be incorporated within a single housing, or the devices may be separately housed but physically and proximately connected.

Figure 2A:
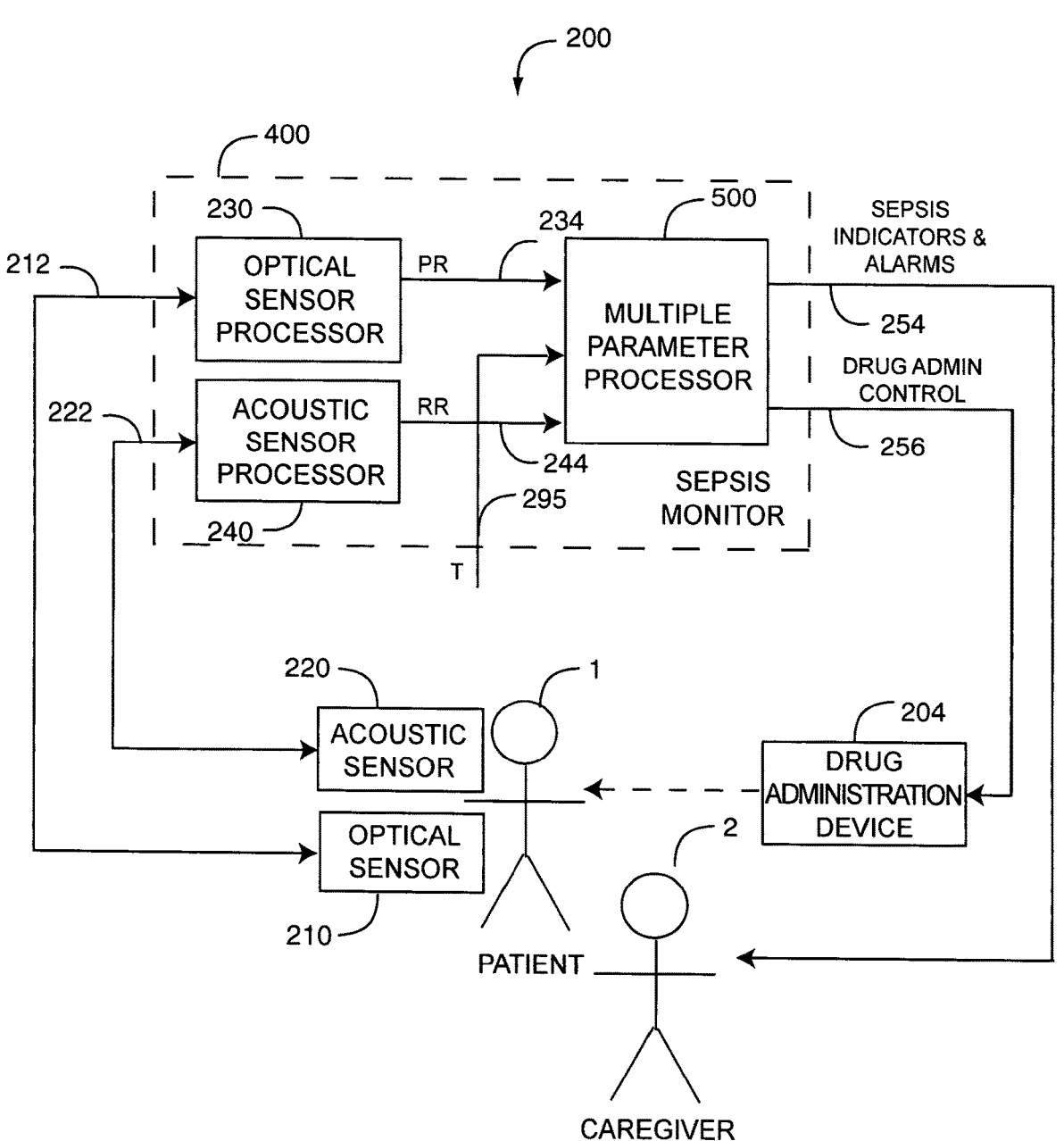
FIGS. 2A-B are detailed diagrams of sepsis monitoring system embodiments.
Figure 2B:
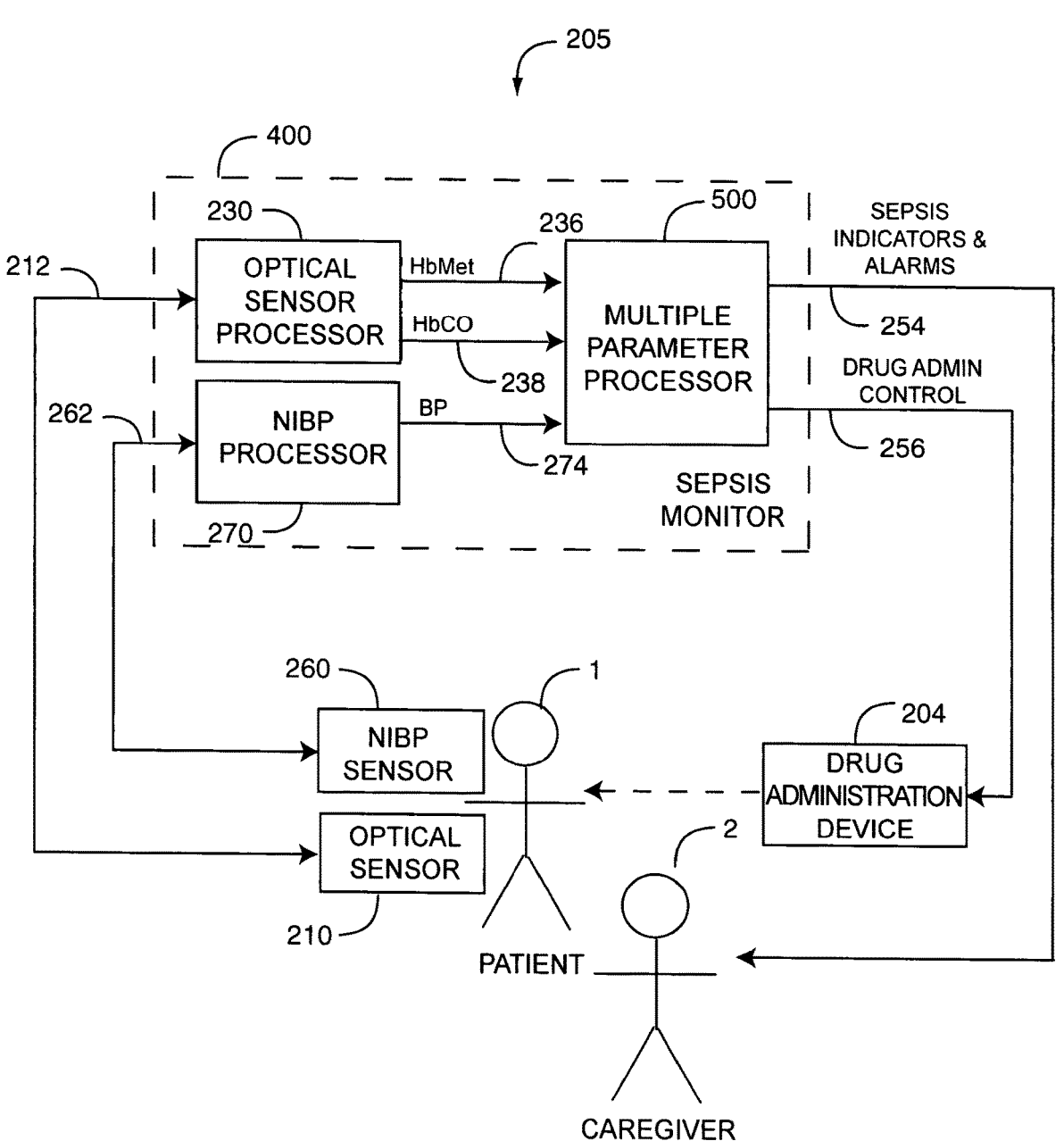

FIGS. 2A-B illustrate sepsis monitoring system embodiments 200, 205. As shown in FIG. 2A with respect to a system embodiment 200, a sepsis monitor 400 is in communications with an optical sensor 210 and an acoustic sensor 220 attached to a patient 1. An optical sensor processor 230 generates pulsatile-blood related parameters, such as pulse rate (PR) 234, in response to optical sensor signals 212. An acoustic sensor processor 240 generates body-sound related parameters 244, such as respiration rate (RR), in response to acoustic sensor signals 222. A temperature parameter 295 is generated via a temperature sensor or manually entered. A multiple parameter processor 500 processes the parameter measurements 234, 244, 295 alone or in combination and generates sepsis indicators and alarms 254 or drug administration controls 256, or both, in response. An acoustic sensor is described in U.S. Pat. No. 6,661,161 entitled Piezoelectric Biological Sound Monitor with Printed Circuit Board and a corresponding respirator rate monitor is described in International App. No. PCT/CA2005/000536 and PUb. No. WO 2005/096931, filed Apr. 8, 2005, both applications incorporated by reference herein.

As shown in FIG. 2B with respect to a system embodiment 205, a sepsis monitor 400 is in communications with an optical sensor 210 and a NIBP sensor 260 attached to a patient 1. An optical sensor processor 230 generates pulsatile-blood related parameters, such as such as HbCO 236 and HbMet 238 in response to optical sensor signals 212. An NIPB processor 270 generates blood pressure (BP) parameters, in response to NIBP sensor signals 262. A multiple parameter processor 500 processes the parameter measurements 236, 238, 274 alone or in combination and generates sepsis indicators and alarms 254 or drug adminstration controls 256, or both, in response. A continuous NIBP (CNIBP) sensor and processor are described in U.S. Pat. No. 5,590,649 entitled Apparatus and Method for Measuring an Induced Perturbation to Determine Blood Pressure and an intelligent cuff inflation (ICI) sensor and processor are described in U.S. Pat. No. 5,785,659 entitled Automatically Activated Blood Pressure Measurement Device, both patents incorporated by reference herein.

Advantageously, the multiple parameter processor 500 is responsive to a combination of multiple physiological parameters to indicate sepsis so that an alert can be provided based upon these parameters. Further, the multiple parameter processor 500 responds not only to parameter limits but also to parameter trend information, parameter patterns and parameter variability, so as to reflect a patient condition over time. In an embodiment, sepsis indicators 254 include alarms and wellness indicators that indicate stages of sepsis from none, to the onset of sepsis, to severe sepsis and septic shock. These outputs, for example, provide a warning of a potential onset of sepsis at an early stage and can trigger alarms as sepsis symptoms progress. Further, drug administration control 256 controls the administration of drugs or alters drug doses in response to patient condition. In an embodiment, the multiple parameter processor 500 compares parameter limits and rising or falling trends of the measurements 234, 244, 236, 238, 274, 295 alone or in combination, with corresponding predetermined thresholds and generates indicators and alarms 254 or drug administration controls 256 in response. The comparisons utilize a rule-based metric analysis, as described in detail in respect to FIGS. 4-5, below.

In one embodiment, the sepsis indicators 254 include a green indicator signaling a stable condition, a yellow indicator signaling a less stable condition or a potential sepsis onset and a red indicator signaling an unstable or severe sepsis condition. The indicators 254 may be, for example, various display LEDs emitting wavelengths of the appropriate colors. In an embodiment, a sepsis monitor 400 provides indicators 254 according to TABLES 1 and 2 below.

In an embodiment according to TABLE 1, below, if a patient's pulse rate (PR) and respiration rate (RR) are less than predetermined maximum limits and their body temperature is within a predetermined normal range, then the sepsis monitor 400 displays a green indicator. However, if more than one of pulse rate, respiration rate and body temperature are changing, where applicable changes in pulse rate and respiration rate are rate increases, then the sepsis monitor 400 displays a yellow indicator, signaling a potential onset of sepsis. If more than one of pulse rate, respiration rate and temperature become abnormal, including pulse rate and respiration rate above a predetermined limit and temperature outside of a predetermined range, then the sepsis monitor 400 displays a red indicator, signaling a potential sepsis condition.

TABLE 1

| Rule-Based Monitor Outputs | |
| --- | --- |
| RULE | OUTPUT |
| If PR < heart rate limit; RR < breathing rate limit; & T in normal range. | Then illuminate green indicator. |
| If PR rising > heart rate trend limit; RR rising > breathing rate trend limit; & T rising or fallina. | Then illuminate yellow indicator |
| If PR > heart rate limit; RR > breathing rate limit; & T outside normal range. | Then illuminate red indicator; Trigger audible alarm. |

In an embodiment according to TABLE 2, below, if a patient's carboxyhemoglobin (HbCO), methemeglobin (HbMet) and blood pressure (BP) are normal, i.e. HbCO and HbMet less than predetermined maximum limits and BP greater than a predetermined minimum limit, then the sepsis monitor 400 displays a green indicator. However, if any of HbCO, HbMet and BP are changing, where applicable changes in HbCO and HbMet are increases and the applicable change in BP is a decrease, then the sepsis monitor 400 displays a yellow indicator, signaling a potential onset of sepsis. If any of HbCO, HbMet and BP change beyond predetermined limits, then the sepsis monitor 400 displays a red indicator, signaling a potential sepsis condition.

TABLE 2

| Additional Rule-Based Monitor Outputs | |
| --- | --- |
| RULE | OUTPUT |
| If HbCO < CO limit; HbMet < Met limit; & BP > blood pressure limit. | Then illuminate green indicator. |
| If HbCO rising > CO trend limit; HbMet rising > Met trend limit or BP falling. | Then illuminate yellow indicator |
| If HbCO > HbCO limit threshold; HbMet & > HbMet limit threshold; or BP < blood pressure limit. | Then trigger an alarm, such as An audible or a visual alert or both. |

In other embodiments, a sepsis monitor 400 utilizes predetermined limits and ranges on any or all of PR, RR, T, HbCO, HbMet and BP to indicate no sepsis, a potential onset of sepsis or a sepsis condition, with green, yellow and red indicators or with other visual and audible indicators, displays and alarms. Other indicators, alarms, controls and diagnostics in response to various combinations of parameters and thresholds can be substituted for, or added to, the rule-based outputs illustrated in TABLES 1 and 2.

Other parameter measurements that may be input to the multiple parameter processor 500 include oxygen saturation (SpO$_2$) and perfusion index (PI) as derived from a pulse oximeter, EGG, EEG and ETCO$_2$, to name a few. All of these parameters may indicate real-time measurements and historical data such as measurement trends, patterns and variability. Signal quality measurements may also be input to the multiple parameter processor 500. Pulse oximetry signal quality and data confidence indicators are described in U.S. Pat. No. 6,684,090 entitled Pulse Oximetry Data Confidence Indicator, a pattern recognition alarm indicator is described in U.S. Pat. No. 6,822,564 entitled Parallel Measurement Alarm Processor, both patents assigned to Masimo Corporation, Irvine, GA and incorporated by reference herein.

Figure 3:
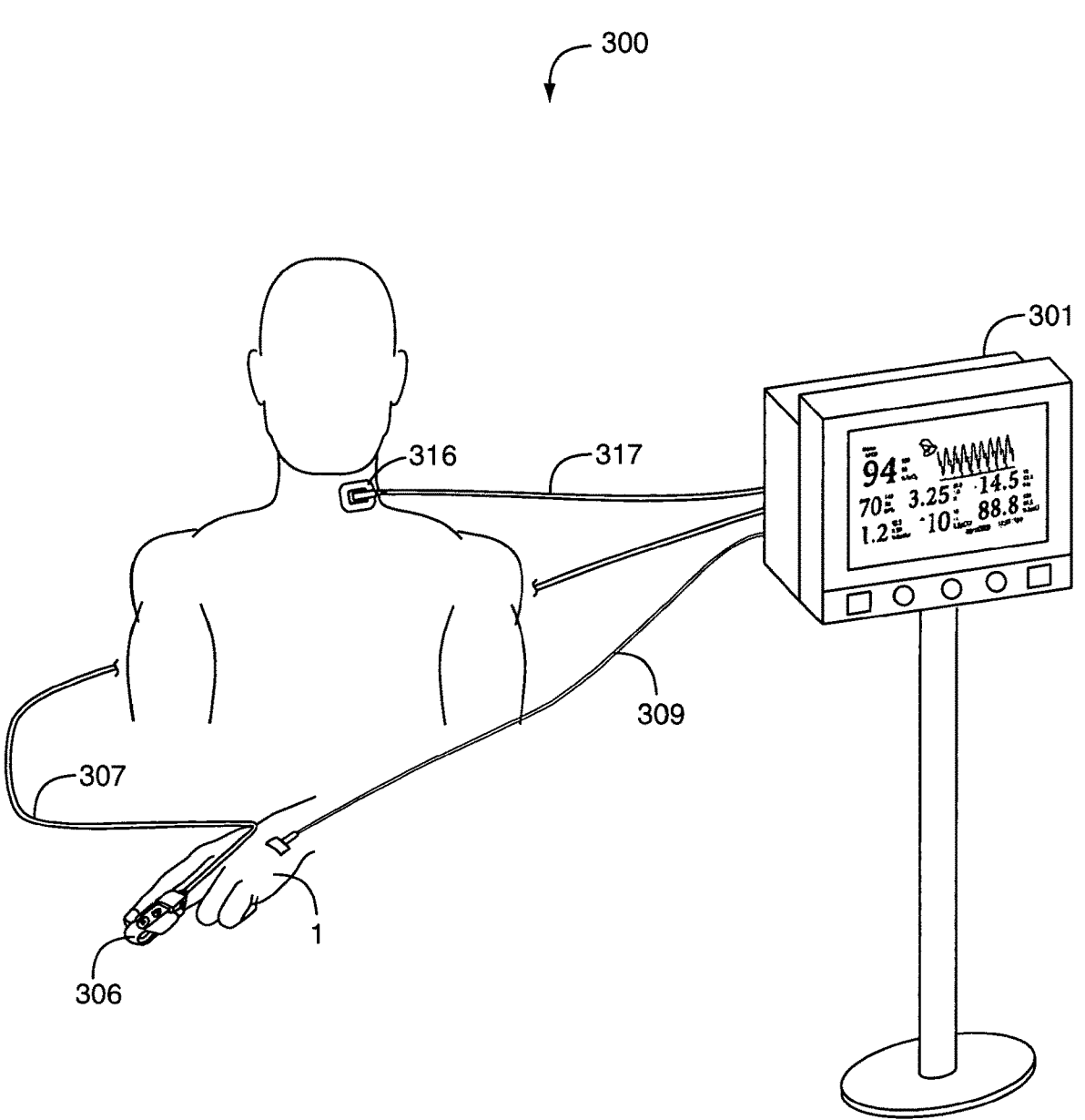
FIG. 3 is an illustration of a sepsis monitoring system embodiment.

FIG. 3 illustrates a sepsis monitoring system 300 combining a sepsis monitor 400 (FIG. 1) and a drug administration device 204 (FIGS. 2A-B) into a drug infusion monitor 301. The sepsis monitoring system 300 has an optical sensor 306 and a piezoelectric sensor 316 attached to a patient's body 1. The optical sensor 306 detects pulsatile blood components and the piezoelectric sensor 316 detects tracheal sounds. The corresponding optical and acoustic sensor signals are transmitted to the drug infusion monitor 301 via an optical-sensor cable 307 and an acoustic-sensor cable 317. The drug infusion monitor 301 generates blood parameter measurements such as PR, HbCO and HbMet and biological sound measurements such as respiration rate (RR) and processes the measurements to display sepsis indicators and administer corresponding treatments. In a particular embodiment, the drug infusion monitor 301 intravenously administers one or more drugs, such as recombinant activated protein C, to the patient 1 in doses and dose intervals so as to respond to varying stages of sepsis or the potential onset of sepsis and to transitions between less severe and more severe stages of sepsis.

Figure 4:
FIG. 4 is a general block diagram of a sepsis monitor incorporating a multiple parameter processor.
Figure 4:
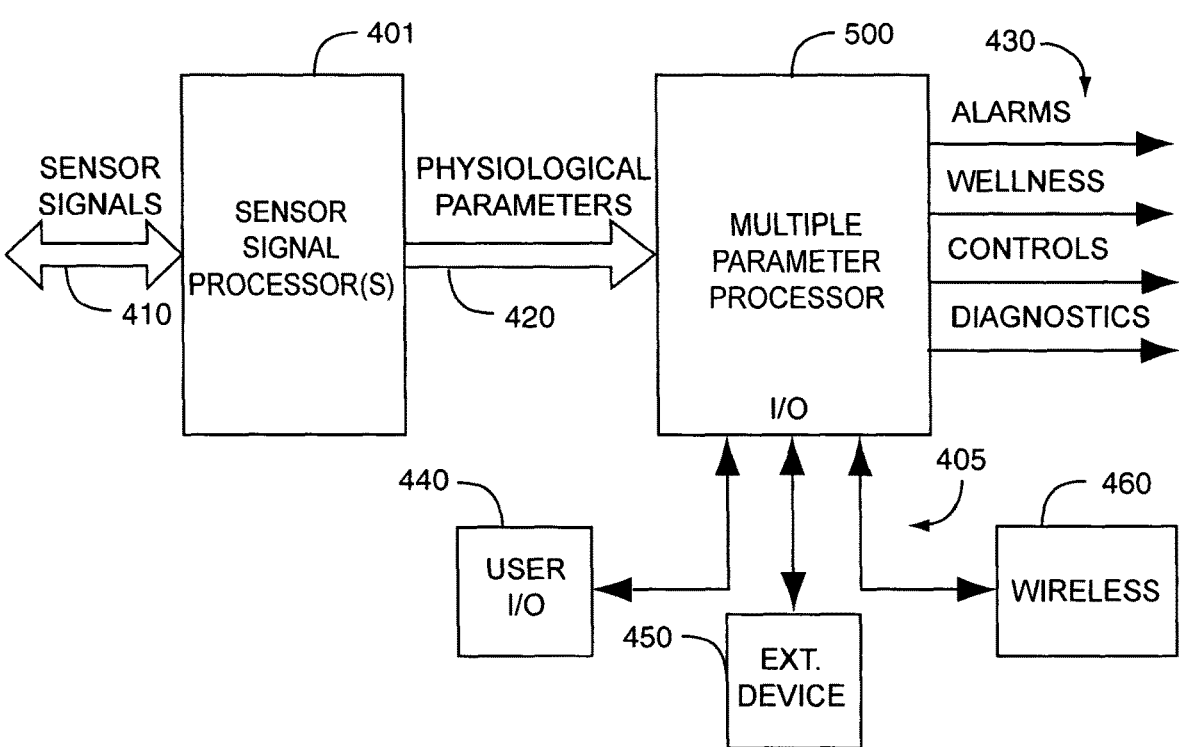

FIG. 4 illustrates a sepsis monitor embodiment 400 having sensor signal processor(s) 401, a multiple parameter processor 500, sensor signal inputs 410 to the signal processor(s) 401 and monitor outputs 430 from the parameter processor 500. Monitor outputs 430 may be sepsis alarms, wellness indicators, controls and sepsis diagnostics. Alarms may be used to alert medical personnel to a potential urgent or emergency medical condition in a patient under their care. Wellness indicators may be used to inform medical personnel as to patient condition stability or instability, such as a less urgent but potentially deteriorating medical state or condition. Diagnostics may be messages or other indicators used to assist medical personnel in diagnosing or treating a patient condition. Controls may be used to affect the operation of a medical treatment device, as described above, or other medical-related equipment.

In an embodiment, the multiple parameter processor 500 also has an input and output port (I/O) 405 that provides communications to the outside world. The I/O includes user I/O and external device communications to name a few. User I/O allows manual data entry and control. For example, a menu-driven operator display may be provided to allow entry of predetermined alarm thresholds. External device communications may include interfaces, networks or wireless communications to PCs, printers, chart recorders or displays to name a few.

Figure 5:
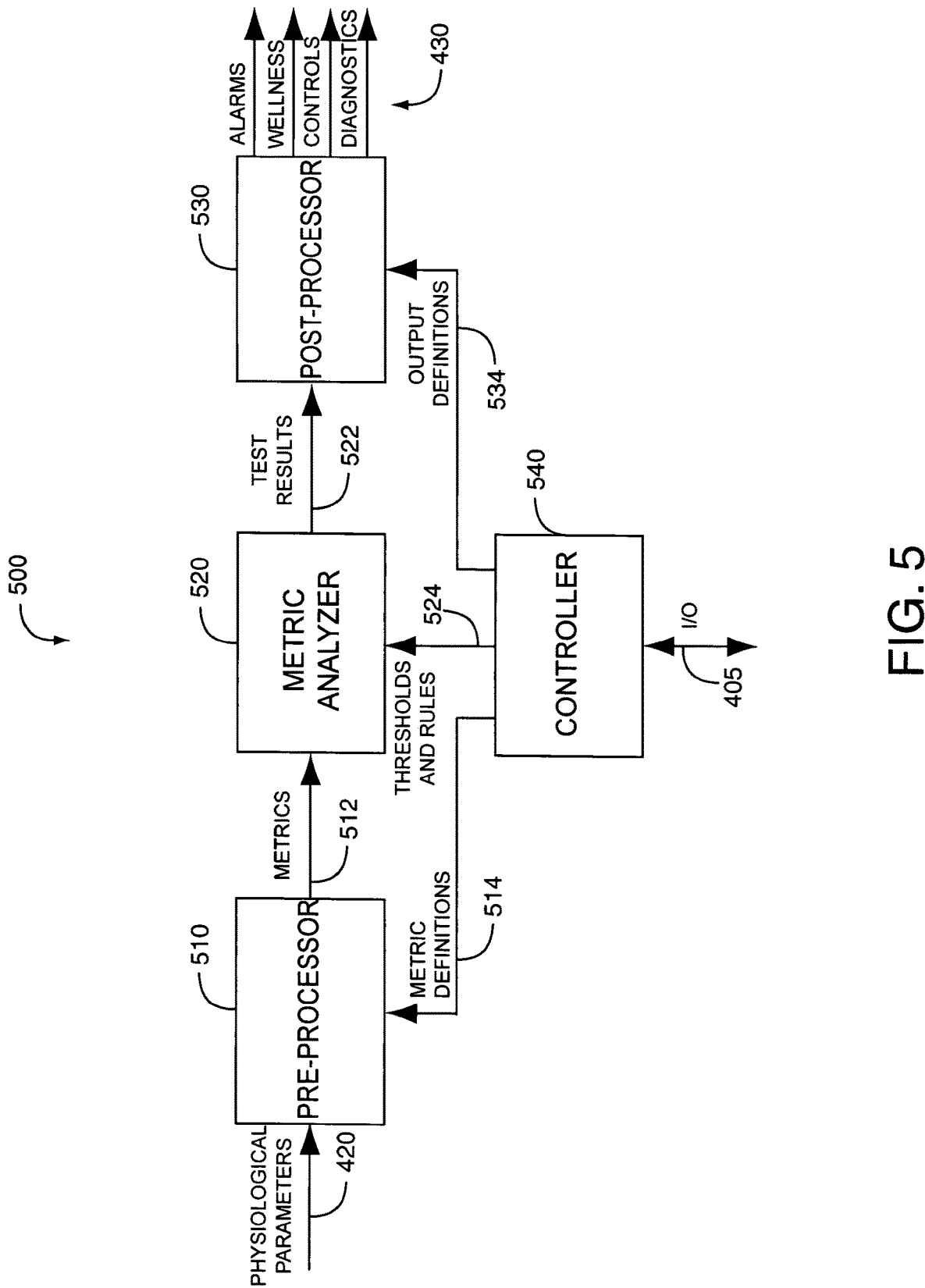
FIG. 5 is a detailed block diagram of a multiple parameter processor embodiment.

FIG. 5 illustrates a sepsis monitor embodiment 500 having a pre-processor 510, a metric analyzer 520, a post-processor 530 and a controller 540. The pre-processor 510 has inputs 420 that may be real-time physiological parameter measurements, historical physiological parameter measurements, signal quality measures or any combination of the above. The pre-processor 510 generates metrics 512 that may include historical or real-time parameter trends, detected parameter patterns, parameter variability measures and signal quality indicators to name a few. As examples, trend metrics may indicate if a physiological parameter is increasing or decreasing at a certain rate over a certain time, pattern metrics may indicate if a parameter is cyclical within a particular frequency range or over a particular time period, variability metrics may indicate the extent of parameter stability.

As shown in FIG. 5, the metric analyzer 520 is configured to provide test results 522 to the post-processor based upon various rules applied to the metrics 512 in view of various thresholds 524. As an example, the metric analyzer 520 may output an alarm trigger 522 to the post-processor 530 when a parameter measurement 503 increases faster than a predetermined rate. This may be expressed, as an example, by a rule that states "if trend metric exceeds trend threshold then trigger alarm." TABLE 1 and TABLE 2, above, illustrate sepsis monitor rules applied to metrics including PR, RR, T, HbCO, HbMet and BP parameters and trends.

Also shown in FIG. 5, the post processor 530 inputs test results 522 and generates outputs 502 including alarms, wellness indictors, controls and diagnostics. Alarms may be, for example, audible or visual alerts warning of critical conditions that need immediate attention. Wellness indicators may be audible or visual cues, such as an intermittent, low-volume tone or a red/yellow/green light indicating a patient with a stable or unstable physiological condition, as examples. Controls may be electrical or electronic, wired or wireless or mechanical outputs, to name a few, capable of interfacing with and affecting another device. Diagnostics may indicate a particular patient condition, such as the potential onset of sepsis.

Further shown in FIG. 5, the controller 540 interfaces with I/O 509. In one embodiment, the I/O 509 provides predetermined thresholds, which the controller 540 transmits to the metric analyzer 520. The controller 540 may also define metrics 514 for the pre-processor 510 and define outputs 534 for the post-processor 530.

A sepsis monitor has been disclosed in detail in connection with various embodiments. These embodiments are disclosed by way of examples only and are not to limit the scope of the claims that follow. One of ordinary skill in art will appreciate many variations and modifications.

What is claimed is:

1. A wellness monitor configured to alarm at an onset of a sepsis condition through monitoring a pulse rate, respiration rate and temperature of a wearer, the wellness monitor comprising:

one or more sensors configured to be applied to a wearer, the one or more sensors configured to output a plurality of signals responsive to noninvasive measurements, one or more of the plurality of signals including data sufficient to determine a pulse rate, a respiration rate and a temperature of the wearer;

one or more processors configured to receive and process said data, electronically determine said pulse rate, said respiration rate, and said temperature, and output a sepsis alarm responsive to said determination, said processing including comparing measurement values and comparing measurement trends, wherein said comparing measurement values comprises determining if all of a set of first conditions are met contemporaneously, the set of first conditions comprising: (i) said pulse rate being above a pulse rate threshold, (ii) said respiration rate being above a respiration rate threshold, and (iii) said temperature being above a high temperature threshold or being below a low temperature threshold, and wherein said comparing measurement trends comprises determining if all of a set of second conditions are met contemporaneously the set of second conditions comprising: (a) a pulse rate trend of said pulse rate rising over a first predetermined time interval and exceeding a pulse rate trend limit, (b) a respiration rate trend of said respiration rate rising or being above said respiration rate threshold over a second predetermined time interval and exceeding a respiration rate trend limit, and (c) a temperature trend rising relative to a high temperature threshold or said temperature trend falling relative to a low threshold, wherein said pulse rate threshold corresponds to an abnormal pulse rate, said respiration rate threshold corresponds to an abnormal respiration rate, and said high and low temperature thresholds each correspond to respective abnormal temperatures, and wherein said sepsis alarm comprises tiered outputs including a first output generated when the first set of conditions are met and a second output generated when the second set of conditions are met, wherein the first output conveys a higher severity level than the second output via a multi-modal set of indicators, wherein, when conditions for both the first set and the second set are met, the monitor is configured to present the first output and not the second output.

2. The monitor of claim 1, wherein said one or more sensors comprises a noninvasive pulse oximetry sensor.

3. The monitor of claim 2, wherein said one or more processors are further configured to output a drug control signal configured to cause a drug administration device to one of deliver medication to said wearer, adjust a delivery of medication to said wearer or cease the delivery of medication to said wearer.

4. The monitor of claim 1, wherein said one or more processors are further configured to output a drug administration instruction to a caregiver, said instruction configured to inform the caregiver about the administration of medication to said wearer.

5. The monitor of claim 1, wherein said first set of conditions comprises a potential sepsis condition and said second set of conditions comprises a potential sepsis condition.

6. A multiple parameter processor configured to generate alarms, a first alarm corresponding to a set of specific physiological parameter measurements all being abnormal, a second alarm corresponding to a set of specific trends of physiological parameter measurements all being abnormal, the first and second alarms being different flags of a sepsis condition of a wearer of noninvasive sensors including at least a noninvasive pulse oximetry sensor, the processor comprising:

a first electronic signal input responsive to a currently monitored pulse rate of the wearer;

a second electronic signal input responsive to a currently monitored respiration rate of the wearer;

a third electronic signal input responsive to a currently monitored temperature of the wearer;

a first electronic output configured to generate the first alarm, the first alarm corresponding to when all of a set of first conditions related to pulse rate, respiration rate, and temperature of the wearer are met, the set of first conditions comprising: (i) said pulse rate being above a pulse rate threshold corresponding to an abnormal pulse rate, (ii) said respiration rate being above a respiration rate threshold corresponding to an abnormal respiration rate, and (iii) said temperature being above a high temperature threshold or being below a low temperature threshold, the high and low temperature thresholds corresponding to abnormal temperatures; and a second electronic output configured to generate the second alarm, the second alarm corresponding to when all of a set of second conditions related to pulse rate, respiration rate, and temperature of the wearer are met, the set of second conditions comprising: (a) a pulse rate trend of said pulse rate rising over a respective predetermined time interval and exceeding a pulse rate trend limit, (b) a respiration rate trend of said respiration rate rising over a respective predetermined time interval and exceeding a respiration rate trend limit, and (c) a temperature trend rising relative to a high temperature threshold or said temperature trend falling relative to a low temperature threshold, wherein said first alarm corresponds to a more severe condition than said second alarm, wherein the processor is configured to produce tiered outputs including a first output generated when the first set of conditions are met and a second output generated when the second set of conditions are met, wherein the first output conveys a higher severity level than the second output via a user-perceivable indicator, wherein, when conditions for both the first set and the second set are met, the processor is configured to present only the first output.

7. The processor of claim 6, wherein the first alarm is configured to deliver medication to said wearer, adjust a delivery of medication to said wearer or cease the delivery of medication to said wearer.

8. The processor of claim 6, wherein the second alarm is configured to deliver medication to said wearer, adjust a delivery of medication to said wearer or cease the delivery of medication to said wearer.

9. The processor of claim 6, wherein the first alarm is configured to electronically deliver drug administration instructions to a caregiver.

10. The processor of claim 6, wherein the second alarm is configured to electronically deliver drug administration instructions to a caregiver.

11. The processor of claim 6, wherein said first alarm signals a potential sepsis condition and said second alarm signals a potential sepsis condition.

* * * * *